(12) United States Patent
Gerecht et al.

(10) Patent No.: US 11,530,381 B2
(45) Date of Patent: Dec. 20, 2022

(54) OXYGEN GRADIENT HYDROGEL DRUG SCREENING

(71) Applicants: THE JOHNS HOPKINS UNIVERSITY, Baltimore, MD (US); THE TRUSTEES OF THE UNIVERSITY OF PENNSYLVANIA, Philadelphia, PA (US)

(72) Inventors: Sharon Gerecht, Severna Park, MD (US); Daniel Lewis, Riverside, CT (US); Kyung Min Park, Baltimore, MD (US); T. S. Karin Eisinger, Philadelphia, PA (US); M. Celeste Simon, Philadelphia, PA (US)

(73) Assignees: The Johns Hopkins University, Baltimore, MD (US); The Trustees of the University of Pennsylvania, Philadelphia, PA (US)

( * ) Notice: Subject to any disclaimer, the term of this patent is extended or adjusted under 35 U.S.C. 154(b) by 1004 days.

(21) Appl. No.: 16/323,882

(22) PCT Filed: Jul. 19, 2017

(86) PCT No.: PCT/US2017/042762
§ 371 (c)(1),
(2) Date: Feb. 7, 2019

(87) PCT Pub. No.: WO2018/017657
PCT Pub. Date: Jan. 25, 2018

(65) Prior Publication Data
US 2019/0169563 A1 Jun. 6, 2019

Related U.S. Application Data

(60) Provisional application No. 62/364,379, filed on Jul. 20, 2016.

(51) Int. Cl.
G06K 9/00 (2022.01)
C12M 1/34 (2006.01)
G01N 33/50 (2006.01)

(52) U.S. Cl.
CPC ......... C12M 41/46 (2013.01); G01N 33/5011 (2013.01); G01N 33/5029 (2013.01)

(58) Field of Classification Search
CPC  C12M 41/46; G01N 33/5011; G01N 33/5029
See application file for complete search history.

(56) References Cited

U.S. PATENT DOCUMENTS

2007/0167354 A1    7/2007  Kennedy et al.
2015/0196584 A1*  7/2015  Gerecht .................. A61K 9/06
                                                                     435/68.1

FOREIGN PATENT DOCUMENTS

WO     2001066747 A2    9/2001
WO     2014144932 A2    9/2014

OTHER PUBLICATIONS

Acosta, M., et al., "A microfluidic device to study cancer metastasis under chronic and intermittent hypoxia", Biomicrofluidics 8, 054117 (2014).

(Continued)

*Primary Examiner* — Tom Y Lu
(74) *Attorney, Agent, or Firm* — DLA Piper LLP (US)

(57) ABSTRACT

The present invention describes methods for quantifying and analyzing cell migration and drug screening. Such methods include a gel (or a hydrogel) comprising a polymer, and cells that forms an oxygen gradient within the gel by controlling the balance of the diffusion of oxygen through the top of the gel and by the consumption of oxygen uptake by the cells. The migration of the cells is determined while the cells are grown in the gel of the present invention.

27 Claims, 9 Drawing Sheets

(56) References Cited

OTHER PUBLICATIONS

Debeir, O., et al., "Models of cancer cell migration and cellular imaging and analysis", Transworld Research Network, The Motile Actin System in Health and Disease, 2008:123-156 ISBN: 978-81-7895-333-5.
Jain, P., et al., "Quantitative analysis of random migration of cells using time-lapse video microscopy", J. Vis. Exp. (63), e3585 (2012).
Park, M., et al., "Hypoxia-inducible hydrogels", Nat Commun., (2014), 5: 4075.doi: 10.1038/ncomms5075, pp. 1-26.
Staton, C., et al., "A critical analysis of current in vitro and in vivo angiogenesis assays", Int. J. Exp. Path. (2009), 90, 195-221 doi: 10.1111/j.1365-2613.2008.00633.x.

\* cited by examiner

FIG. 5E  FIG. 5F

OXYGEN GRADIENT HYDROGEL DRUG SCREENING

CROSS-REFERENCE TO RELATED APPLICATIONS

This application is a 35 U.S.C. § 371 U.S. national entry of International Application PCT/US2017/042762, having an international filing date of Jul. 19, 2017, which claims the benefit of U.S. Provisional Application No. 62/364,379, filed Jul. 20, 2016, the content of each of the aforementioned applications is herein incorporated by reference in their entirety.

STATEMENT OF GOVERNMENTAL INTEREST

This invention was made with government support under grant numbers CA153952, and CA158301, awarded by the National Institutes of Health, and grant number 1054415, awarded by the National Science Foundation. The government has certain rights in the invention.

BACKGROUND OF THE INVENTION

Soft tissue sarcomas are a heterogeneous group of malignant cancers derived from transformed cells of mesenchymal origin. Approximately 13,000 new cases per year are diagnosed in the US alone, with 25-50% of patients developing recurrent and metastatic disease. Current clinical data suggest that undifferentiated pleomorphic sarcoma (UPS) is one of the most aggressive sarcoma subtypes, which frequently results in lethal pulmonary metastases that are insensitive to radio/chemotherapy. It has recently become apparent that sarcoma progression and metastasis are regulated by microenvironmental factors such as extracellular matrix (ECM) remodeling, stiffness modulation, cell-to-cell/matrix interactions, signaling factors, tumor vasculature, and spatial gradients. Of all these factors, low intratumoral $O_2$ (hypoxia) is most dramatically associated with pulmonary metastasis, and poor clinical outcomes.

SUMMARY OF THE INVENTION

One embodiment of the present invention is a method for quantifying and analyzing cell migration comprising the following steps: providing a gel comprising a top, a polymer, and cells; and forming an oxygen gradient within the gel by controlling the balance of the diffusion of oxygen through the top of the gel and by the consumption of oxygen uptake by the cells. A suitable gel of the present invention is a hydrogel, or a gel wherein water is the dispersion medium. A suitable oxygen gradient formed within a gel of the present invention is in the range of about 0% to 21%, 1% to 17%, 2% to 15%, 3% to 12%, 4% to 10%, or 5% to 20% of oxygen content. A suitable gel of the present invention further comprises a bottom wherein the cells are located near the bottom or in the bottom ⅔rds of the gel. Typically the gel is in the well of a microtiter plate with the top exposed of oxygen and the bottom along the interior wall of the well of the microtiter plate. Most cells may be suitable for use in the present invention but the preferred cells are cancer cells preferably sarcoma cells, carcinoma cells, or a combination thereof. The cancer cells are preferably obtained from an animal or a human subject and the cells typically deposit their own extracellular matrix in the gel of the present invention. Suitable gel polymers include collagen, gelatin, chitosan, heparin, fibrinogen, hyaluronic acid, chondroitin sulfate, pullulan, xylan, dextran, and polyethylene glycol as well as their derivatives, and combinations thereof. Suitable cross linking agents used to cross link a gel polymer may be selected from the group consisting of physical crosslinkers such as ionic interaction, pH-sensitivity, thermo-sensitivity, stereo-complex, host-guest interaction; chemical cross-linkers such as photo-crosslinking, thiol-ene reaction, michael-type additions, shift-base reaction (glutaraldehyde), Diels-alder reaction; enzyme-mediated cross linkers (laccase, horseradish peroxidase, transglutaminase, tyrosinase, lysyl oxidase or glucose oxidase), catechol oxidations, bis-epoxide; peptide based crosslinkers, or a combination thereof. A cross linking agent of the present invention may be a phenolic agent selected from ferulic acid (FA), tyramine (TA), 4-Hydroxyphenylacetic acid, 3-(4-Hydroxyphenyl) propionic acid, Dopamine, Norepinephrine, epinephrine, and their derivatives. An oxygen gradient of a gel of the present invention is determined by measuring the concentration of dissolved oxygen in at least two regions of the gel using $O_2$ sensors. Any suitable method of analyzing the cells may be used including immunofluorescence staining of the cells as shown in FIGS. 1-6 and the samples. Such analysis enables one to quantify the amount of cell migration when comparing the cell migration of cells within a hydrogel of the present invention having a specific oxygen concentration (or a specific oxygen gradient) as part of a test sample with the cell migration of cells of a reference sample. An example of a suitable reference sample includes cells within a hydrogel of the present invention having an oxygen concentration (or a specific oxygen gradient) different from the test sample.

Another embodiment of the present invention is a method of identifying agents for treating or preventing cancer comprising: providing a gel comprising a top, a polymer, and cancer cells; forming an oxygen gradient by controlling the balance of the diffusion of oxygen through the top of the gel and by the consumption of oxygen uptake by the cells; applying an agent to the gel; and comparing the characteristic of the cancer cells in the gel to reference cancer cells in a reference gel wherein the agent has not been applied to the reference gel or reference cells. Suitable characteristics include gene expression, protein expression, cytoskeleton organization, nucleus shape, cell shape, ECM secretion and assembly, matrix degradation, matrix remodeling or a combination thereof. A preferred characteristic is gene expression, wherein the mRNA expression is measured of a gene selected from the group comprising HIF-1α, ColA1, LOX, PLOD2, or a combination thereof. Another preferred characteristic is cell migration wherein the cell migration is determined by taking images of different regions within the hydrogels and using cell tracking to measure the distance from the edge of the tumor to the end of the tumor invading the gel. A suitable method of determining the cell tracking is by confocal z-stack analysis. The reference hydrogel may be a non-hypoxic hydrogel having a dissolved oxygen content of greater than 5%. The gels of the present invention may have a thickness in the range of about 1.0 mm to 4.0 mm, 1.5 mm to 4.5 mm, 2.0 mm to 5.0 mm or 2.0 mm to 6.0 mm. A suitable agent of the present invention may include a capture molecule, protein, peptide, nucleic acid, chemical, or a combination thereof. A suitable capture molecule may include an antibody, an antibody fragment, an aptamer, a monoclonal antibody, or a combination thereof.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "anti-GAPDH antibody" is meant an antibody that selectively binds a GAPDH polypeptide.

By "anti-PLOD2 antibody" is meant an antibody that selectively binds a PLOD2 polypeptide.

By "disease" is meant any condition or disorder that damages or interferes with the normal function of a cell, tissue, or organ. Examples of diseases include pancreatic cancer.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "Hybridization" is meant hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "marker" is meant any protein or polynucleotide having an alteration in expression level or activity that is associated with a disease or disorder. The term "biomarker" is used interchangeably with the term "marker."

The term "measuring" means methods which include detecting the presence or absence of marker(s) in the sample, quantifying the amount of marker(s) in the sample, and/or qualifying the type of biomarker. Measuring can be accomplished by methods known in the art and those further described herein, including but not limited to immunoassay. Any suitable methods can be used to detect and measure one or more of the markers described herein. These methods include, without limitation, ELISA and bead-based immunoassays (e.g., monoplexed or multiplexed bead-based immunoassays, magnetic bead-based immunoassays).

As used herein, "obtaining" as in "obtaining an agent" includes synthesizing, purchasing, or otherwise acquiring the agent.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

By "reduces" is meant a negative alteration of at least 10%, 25%, 50%, 75%, or 100%.

By "reference" is meant a standard or control condition.

By "Immunoassay" is meant an assay that uses an antibody to specifically bind an antigen (e.g., a marker). The immunoassay is characterized by the use of specific binding properties of a particular antibody to isolate, target, and/or quantify the antigen.

The term "antibody," as used in this disclosure, refers to an immunoglobulin or a fragment or a derivative thereof, and encompasses any polypeptide comprising an antigen-binding site, regardless of whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, $F(ab')_2$, Fv, scFv, Fd, dAb, and other antibody fragments that retain antigen-binding function, i.e., the ability to bind, for example, PD-L1, specifically. Typically, such fragments would comprise an antigen-binding domain.

The terms "antigen-binding domain," "antigen-binding fragment," and "binding fragment" refer to a part of an antibody molecule that comprises amino acids responsible for the specific binding between the antibody and the antigen. In instances, where an antigen is large, the antigen-binding domain may only bind to a part of the antigen. A portion of the antigen molecule that is responsible for specific interactions with the antigen-binding domain is referred to as "epitope" or "antigenic determinant." An antigen-binding domain typically comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

Binding fragments of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in a F(ab')2 fragment in which the two arms of the antibody molecule remain linked and comprise two-antigen binding sites. The F(ab')2 fragment has the ability to crosslink antigen. "Fv" when used herein refers to the minimum fragment of an antibody that retains both antigen-recognition and antigen-binding sites. "Fab" when used herein refers to a fragment of an antibody that comprises the constant domain of the light chain and the CHI domain of the heavy chain.

The term "mAb" refers to monoclonal antibody. Antibodies of the invention comprise without limitation whole native antibodies, bispecific antibodies; chimeric antibodies; Fab, Fab', single chain V region fragments (scFv), fusion polypeptides, and unconventional antibodies.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, the term "subject" refers to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, the term "range" is understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any compositions or methods provided herein can be combined with one or more of any of the other compositions and methods provided herein.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

BRIEF DESCRIPTION OF THE DRAWINGS

FIG. 5(A)-5(G) illustrates minoxidil inhibit sarcoma cell migration and matrix remodeling in hypoxic hydrogel. KIA-GFP cells were tracked on day 3 in hypoxic treated and untreated hydrogel to determine (A) Three-dimensional trajectories of tracked cells (representative trajectories), (B) Overall speed (C) Velocity in the x, y, and z directions; and (D) Mean square displacement (MSD) in the x, y, and z directions. Plots were created using position of KIA-GFP cells in the hydrogels. (E) Collagen deposition and quantification (collagen in red; nuclei in blue). Scale bars, 50 μm. (F) Proteolytic degradation of HI hydrogels incorporating DQ™ gelatin for 3 days: (i) Representative fluorescence microscopy images. Scale bars, 20 μm and (ii) Quantitative analysis of relative fluorescence intensity (RFU). (G) Western blot analyses for PLOD2 in KIA cells cultured in hypoxic conditions with and without minoxidil treatment. Significance levels were set at *P<0.05, ^P<0.01 and #P<0.001.

DETAILED DESCRIPTION OF THE INVENTION

Figure 1A:
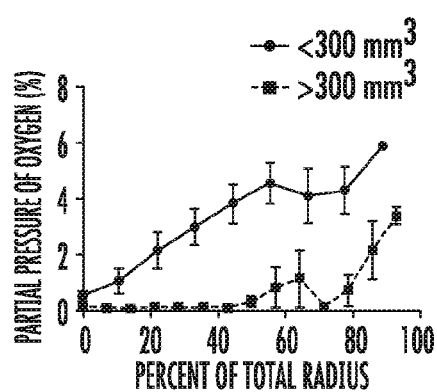
FIG. 1A-1G illustrates enhanced invasion of sarcoma tumor grafts in hypoxic hydrogels. (A) In situ DO measurements in KIA tumors. (B) H&E stains and (C) HIF1-α stains (left) and quantification (right) of small and large tumors. Scale bars, 200 μm for the 4× images and 20 μm for the 40× images. (D) Schematic illustration of tumor encapsulation within HI hydrogel matrix. (E) DO levels of HI hydrogels encapsulated with tumor biopsy in hypoxic and nonhypoxic matrixes up to day 7 in culture (F) Left: Light microscope (left) and fluorescence microscope (right) images of sarcoma tumors encapsulated within nonhypoxic and hypoxic matrices (phalloidin in green; nuclei in blue). H, hydrogels; T, tumors. Scale bars, 100 μm. Right: Quantitative analysis of the sarcoma tumor invasion into hydrogel matrix, (G) Immunofluorescence staining and quantification of collagen deposition by tumor grafts cultured for 7 days (collagen in red; nuclei in blue). Scale bars, 25 μm. Significance levels were set at *P<0.05, P<0.01 and *P<0.001.

Intratumoral hypoxia occurs when the partial pressure of $O_2$ falls below 5% and is a commonly observed feature of many sarcomas. Regional hypoxia develops as rapidly growing tumors outstrip their blood supply and as a consequence of aberrant tumor angiogenesis. As a result, $O_2$ gradients develop throughout the growing tumor. Tumor hypoxia promotes chemo- and radiation resistance, primarily due to limited perfusion and reduced generation of reactive oxygen species (ROS), respectively. Moreover, the stabilization and activation of Hypoxia Inducible Factor (HIF) transcriptional regulators promotes adaptation to hypoxic stress by modulating tumor cell metabolism, survival, angiogenesis, migration, invasion, and metastasis. Elevated HIF expression has been associated with poor prognosis in many cancers and correlates with reduced survival for sarcoma patients. Recent transcriptome analyses have identified HIFs and HIF target genes as independent prognostic indicators of clinical outcomes. Finally, high levels of intratumoral hypoxia and HIF1-α accumulation are among the most important predictors of metastatic potential in patients with sarcoma, although the underlying mechanisms for this correlation remain incompletely characterized. Importantly, while the effect of overall reduced $O_2$ on sarcoma cell responses has been studied; these cells are actually subjected to $O_2$ gradients. Currently, the impact of specific oxygen gradients on sarcoma cell migration is unclear.

The inventors found that deposition of immature collagen networks facilitated tumor cell metastasis to the lung in a HIF-1α dependent manner. The inventors also demonstrated that the HIF-1α regulated sarcoma metastasis through upregulation of procollagen-lysine, 2-oxoglutarate 5-dioxygenase (PLOD2) and the resulting increase in lysine hydroxylation of collagen molecules. The inventors have shown that PLOD2 expression promotes metastasis in a hypoxia- and HIF-1α dependent manner in a genetic in vivo model of UPS. However, the inventors do not yet know how sarcoma cell migration/invasion is altered in the presence of the $O_2$ gradients that develop in tumors.

Using in situ $O_2$ measurements, the inventors found that hypoxia gradients exist in small primary mouse sarcoma tumors while large primary mouse sarcoma tumors contain severe hypoxic cores (≤0.1% $pO_2$). To model intratumoral $O_2$-gradients the inventors used novel $O_2$-controlling hydrogels that can serve as 3D hypoxic microenvironments. In these hypoxia-inducible (HI) hydrogels, $O_2$ is consumed while polymerization occurs resulting in spatial $O_2$ gradients. Thus, with these hydrogels we can mimic physiopathological $O_2$ gradients. By encapsulating small tumor grafts in the hydrogels, we found that hypoxic gradients promoted cell invasion with faster speeds and longer distance, compared to nonhypoxic gradients. The inventors next demonstrate that the HI hydrogel culture system replicates HIF-1α-dependent collagen remodeling by sarcoma cells. Using this system, the inventors then showed that the hypoxic gradients guide the speed, distance, and direction of sarcoma cell motility compared with nonhypoxic hydrogels. Finally, the inventors showed that treatment of the encapsulated sarcoma cells with minoxidil abrogated cell migration and matrix remodeling in the $O_2$ gradient.

Primary Sarcoma Grafts Invade Hypoxic Hydrogels.

Figure 1B:
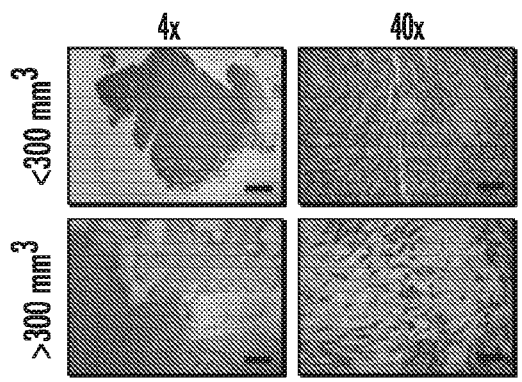
Figure 1C:
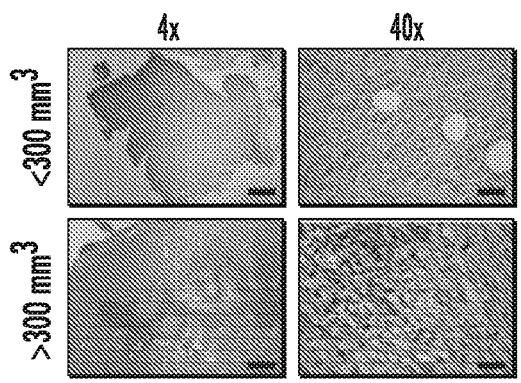
Figure 1D:
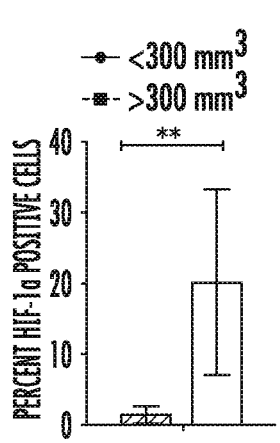
Figure 1D:
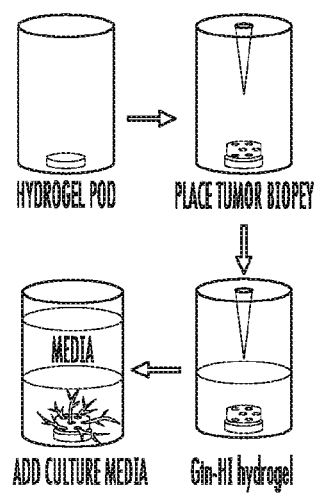
Figure 1E:
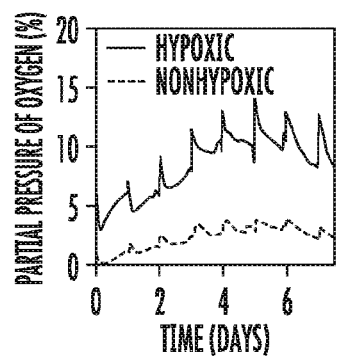
Figure 1F:
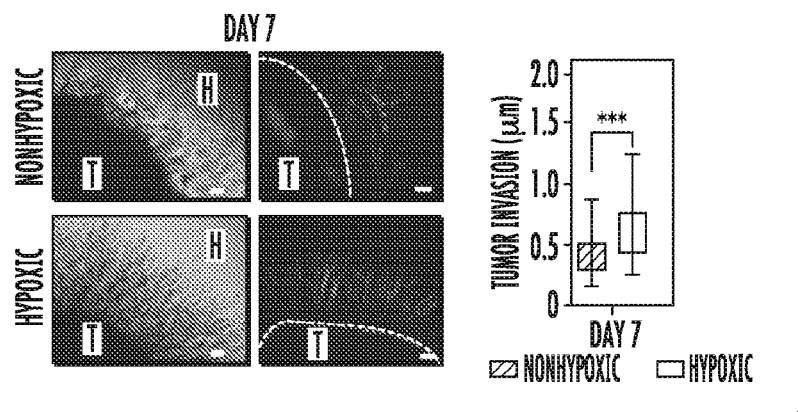
Figure 1G:
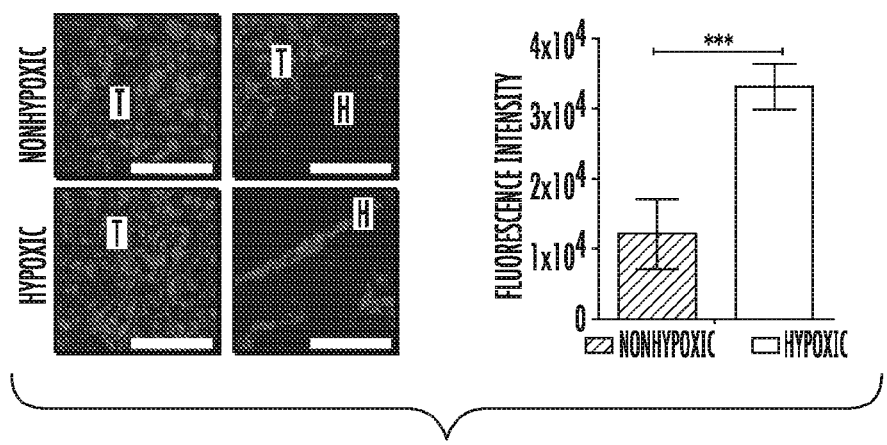

To ascertain the physiological range of $O_2$ gradients in the developing sarcoma tumor, we began by measuring dissolved $O_2$ (DO) levels during the growth of primary mouse sarcoma tumors. The primary sarcoma tumors were generated in nude mice using murine sarcoma cells derived from $Kras^{G12D/+}$; $Ink4a/Arf^{fl/fl}$ tumors (KIA). $O_2$ gradient measurements during growth of subcutaneous primary sarcomas showed that in large tumors (>300 mm$^3$) about 50% of the tumor mass is hypoxic (≤0.1% $pO_2$). Smaller tumors exhibit hypoxic gradients throughout the tumor mass ranging from 0.1% $pO_2$ at the center, to >6% $pO_2$ in the outer layer bordering the edge of the tumor (FIG. 1A). Histological analysis further revealed the severe hypoxic tumor core with cells expressing HIF-1α localized to the nuclei in the larger tumor, while weaker and more diffused HIF-1α signal was observed throughout the entire smaller tumors (FIG. 1B-C). Previously, the inventors have established $O_2$-controlling hydrogels and found that after hydrogel formation, the DO levels at the bottom of hydrogels decreased as gel thickness increased due to oxygen diffusion limitation, resulting in a broad range of $O_2$ tensions within the gel matrices. Based on the oxygen gradient found in the xenograft tumors we sought to use the $O_2$-controllable hydrogel system to provide a more physiologically relevant 3D microenvironment to study cell migration. Using the hypoxic hydrogel system the inventors recreated the hypoxic DO conditions found in the subcutaneous in vivo tumors and evaluated the role of $O_2$ in 3D tumor cell migration assay. Tumor biopsy punches from smaller tumors were cut into 8 mm sections and grafted into the hypoxic and nonhypoxic hydrogels (FIG. 1D). Using noninvasive DO measurements at the bottom of the hydrogels, we found that DO levels in the hypoxic hydrogels reached <5% $pO_2$ within initial 30 min and remained there during the entire week of measurements. Nonhypoxic hydrogels exhibited a higher level of $O_2$ (>5% partial pressure of $O_2$) during this culture period (FIG. 1E). The tumor engrafted within hypoxic matrix demonstrated increased invasion compared with tumors engrafted within nonhypoxic matrix. Specifically, tumors in hypoxic matrix invaded further into the hydrogel and away from the primary graft (after 1 week, 610±210 µm) compared to those encapsulated in nonhypoxic gels (after 1 week, 410±130 µm) (FIG. 1F). Moreover, migrating cells exiting tumor grafts in the hypoxic hydrogel deposited new collagen compared to nonhypoxic hydrogels (FIG. 1G).

Cell Migration from Sarcoma Grafts is Regulated by $O_2$ Gradients.

Figure 2A:
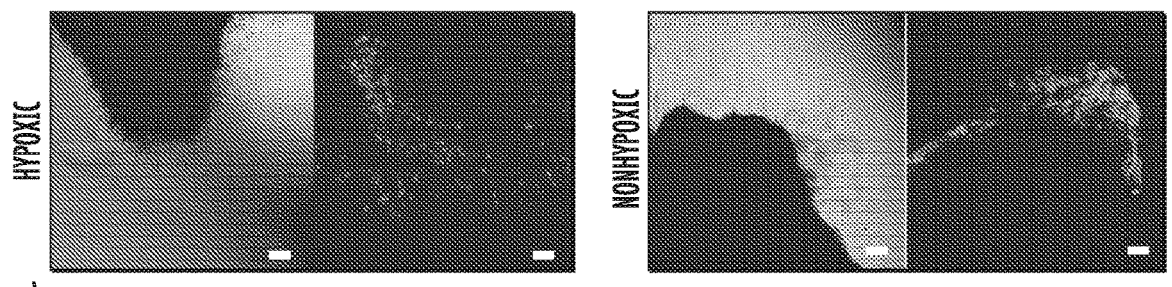
FIG. 2A-2D illustrates hypoxia promote primary sarcoma migration. (A) Light microscope (left) and fluorescence microscope (right) images of day 3 images of KIA-GFP sarcoma tumors encapsulated within nonhypoxic and hypoxic matrices. Migrating GFP cells were tracked to determine (B) Three-dimensional trajectories of tracked cells (representative trajectories) (C) Overall speed, and (D) Mean square displacement (MSD) in the x, y, and z directions. Plots were created using position of KIA-GFP cells in the hydrogels. Significance levels were set at *P<0.05, ^P<0.01 and #P<0.001.
Figure 2B:
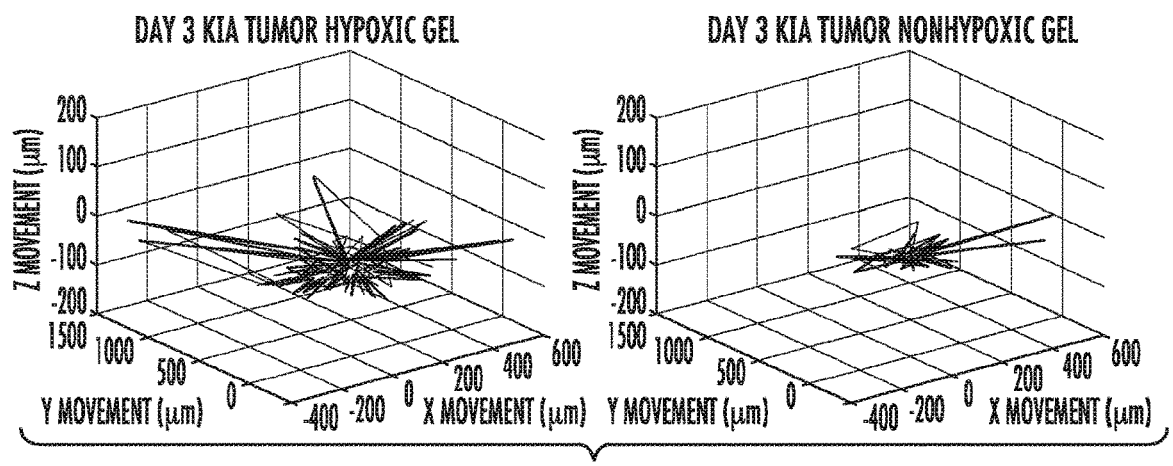
Figure 2C:
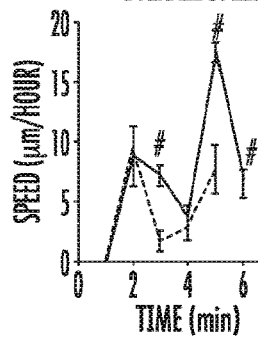
Figure 2D:
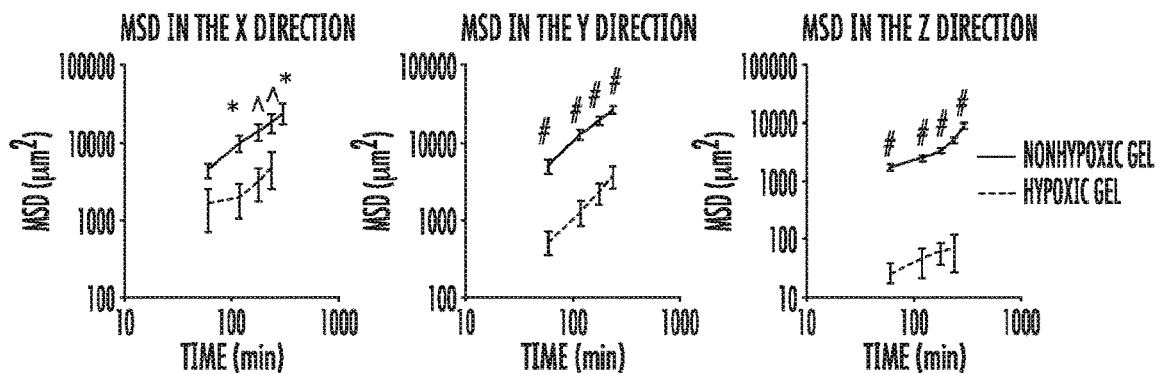

To further investigate the effect of $O_2$ gradients on sarcoma tumor migration, we performed real-time confocal analysis. Tumors generated from green fluorescent protein (GFP) positive KIA cells were engrafted in hypoxic and nonhypoxic hydrogels and imaged on day 3 when we first detected cell invasion into the hydrogel (FIG. 2A). We then analyzed cell migration on day 3, when we could first detect cell invasion from the tumor to the hydrogel. The inventors observed dynamic cell movement in the hypoxic constructs compared to the nonhypoxic constructs with more cells migrating out of the grafts under hypoxic conditions (FIG. 2B). Cell velocity analysis did not indicate specific directionality of migration with most cells moving in the x and y planes, suggesting a random migration path independent of $O_2$ tension. However, we found a higher migration speed in hypoxic grafts compared to nonhypoxic grafts (FIG. 2C). Examining mean square displacement (MSD) in the three planes, we found that cells migrating in the hypoxic gradients move to larger distances compared to the nonhypoxic gradients with significantly longer distance in the z-direction (FIG. 2D) suggesting that while cells typically migrated in the x and y directions, those that migrated in the z-direction exhibited higher persistence. Overall, these data show that hypoxic gradient promotes tumor cell migration.

Sarcoma Cells Remodel Collagen in Hypoxic Hydrogels.

Figure 3A:
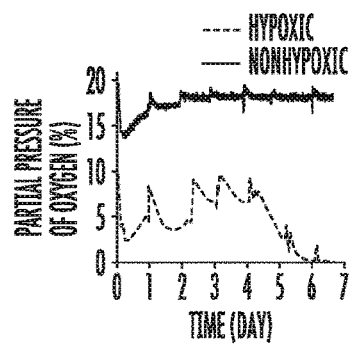
FIG. 3A-3G illustrates Sarcoma cells remodel the hypoxic hydrogel. (A) Non-invasive DO readings at the bottom of the hypoxic and nonhypoxic hydrogel-sarcoma cell constructs. (B) Sarcoma cells encapsulated within HI hydrogels incorporating DQ™ gelatin for 3 days: (i) Representative fluorescence microscopy images. Scale bars, 25 μm and (i)) Quantitative analysis of relative fluorescence intensity (RFU). (C) Young's modulus (Pa) of the hypoxic and nonhypoxic hydrogels on day 0 and after 3 days of culture. (D) Real-time RT-PCR analysis of collagen modification genes. (E) Immunofluorescence staining and analysis of collagen deposition by the encapsulated cells (collagen in red; nuclei in blue). Scale bars, 50 μm. The effect of HIF1-α suppression in encapsulated sarcoma cells (KIA_scr, a control; KIA_HIF-1α(-), HIF knock down) after 7 days in culture was analyzed including: (F) collagen modification gene expression and (G) collagen deposition and quantification (collagen in red; nuclei in blue). Scale bars, 50 μm. Graphical results shown as the average value±s.d. Significance levels were set at *P<0.05, P<0.01 and *P<0.001.
Figure 3B:
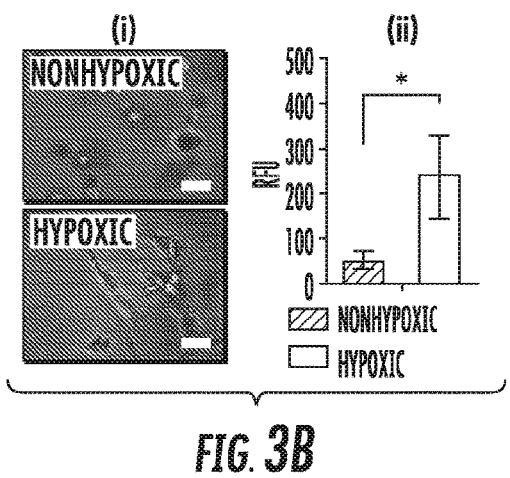
Figure 3C:
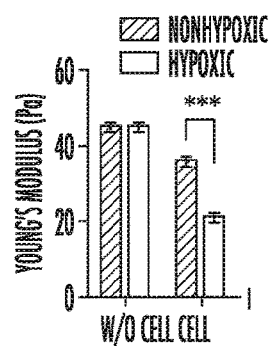
Figure 3D:
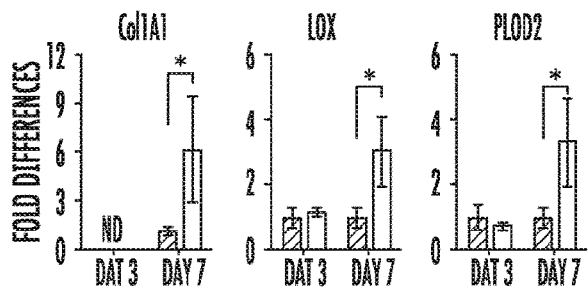
Figure 3E:
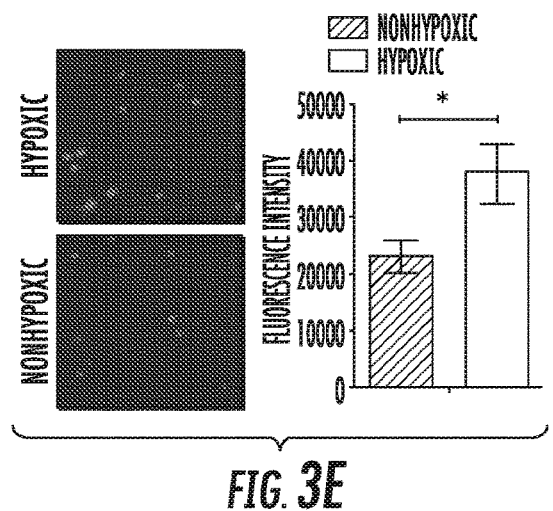
Figure 3F:
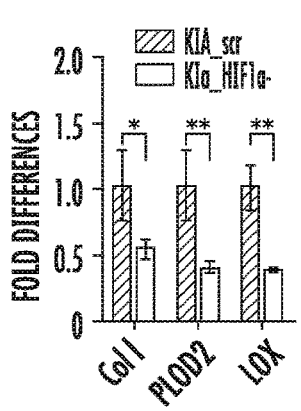
Figure 3G:
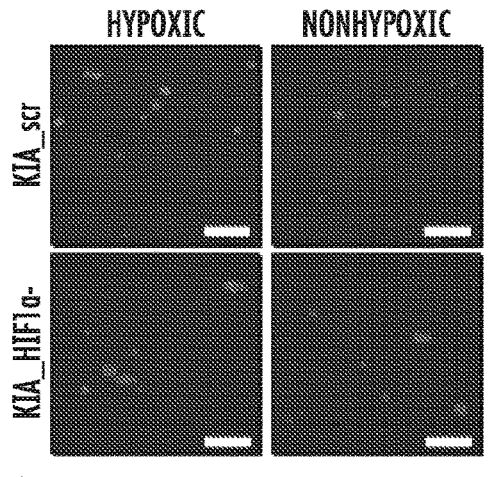

While the tumor graft model provides vital information, the inherited heterogeneity of the system limited the mechanistic insights that such system can provide. To more accurately model the effect of DO gradients on sarcoma cell invasion/migration within a complex tumor microenvironment, we next examined individual sarcoma cells embedded in the HI hydrogel. Non-invasive measurements of DO at the bottom of the hydrogel confirmed that the hypoxic matrix maintains low $O_2$ levels during the 7 days of culture compared to nonhypoxic matrix (FIG. 3A). Notable, by day 7 in culture oxygen levels have decreased to ~0.5%, likely to due to expansion of the cell number over the longer culture period and the associated cellular oxygen consumption. An important feature of this culture system is the ability to maintain the hypoxic gradient environment without exposure to high oxygen levels thus minimizing the introduction of reactive oxygen species (ROS). This, alongside with the ability to perform live-imaging of the cells while monitoring DO levels present a unique opportunity to link cellular responses to DO gradients. Growing evidence suggests that ECM remodeling is critical in sarcoma migration and metastasis. In particular, proteolytic degradation as well as abnormal collagen deposition and modification within hypoxic tumor microenvironments have been implicated as important parameters that enhance tumor invasion and metastasis. The gelatin-based HI hydrogels provide matrix adhesion and degradation sites similar to those in the tumor microenvironment, yet are collagen-free to prevent confounding results. We first tested whether sarcoma cells embedded in hypoxic hydrogel remodel the matrix material. The inventors examined the proteolytic degradation of the HI gelatin matrices using DQ™ gelatin that emits green fluorescence when degraded by a protease secreted by the cells. Interestingly, we observed higher fluorescence intensity in the cells cultured within the hypoxic microenvironments (480 RFU) compared to nonhypoxic matrix (50 RFU) (FIG. 3B). Rheological analysis further confirmed the softening of the hypoxic matrix (young's modulus of 20 Pa) compared to nonhypoxic matrix (young's modulus of 45 Pa) within 3 days of culture (FIG. 3C). The gelatin-based HI hydrogels further enabled us to examine whether sarcoma cells modify collagen in the hypoxic matrix. The inventors next examined the upstream effect of HIF-1α activation on relevant genes on days 3 and 7. While no change in gene expression was detected on day 3 of culture, we observed an upregulation of Col1A1, LOX, and PLOD2 expression after 7 days of culture in the hypoxic hydrogel compared to the nonhypoxic hydrogel (FIG. 3D). Moreover, at this time point, we detected collagen expression and deposition (FIG. 3E) as well as HIF-1α expression by the sarcoma cells in the hypoxic hydrogel. To determine whether ECM remodeling is regulated by the HIF-1α in the hypoxic matrix, we used short hairpin RNA (shRNA). The inventors detected significant down regulation of collagen modifying genes, Col1A1, LOX, and PLOD2 when HIF-1α expression was inhibited (FIG. 3F), resulting in less collagen deposition in hypoxic hydrogel encapsulated cells compared to controls (FIG. 3G). Overall, these results demonstrate that the 3D hypoxic hydrogel, regulates sarcoma matrix remodeling through hypoxic induction of HIF-1α expression. These results are consistent with various sarcoma studies in vivo, suggesting that the HI hydrogels are an appropriate 3D model with the necessary biological attributes to study sarcoma cell invasion and migration.

$O_2$ Gradients Modulate the Speed, Distance and Directional Bias of Sarcoma Cell Motility.

Figure 4A:
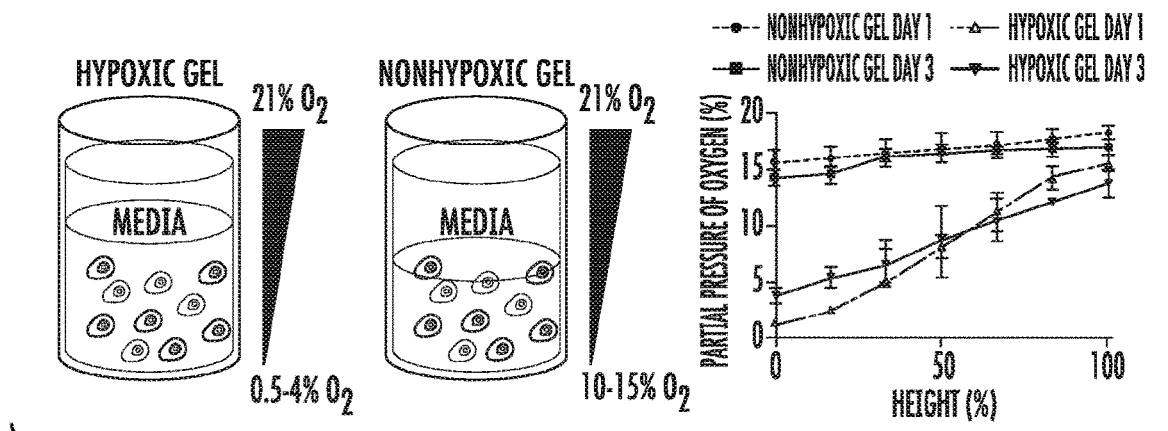
FIG. 4(A)-4(E) illustrates efficient sarcoma cell migration in hypoxic gradients (A) (i)—Illustration of hypoxic and nonhypoxic $O_2$ gradient in HI hydrogels. (ii)—Invasive DO readings showing gradients in the HI hydrogels on Day 1 and 3. KIA-GFP cells were tracked on day 3 in hypoxic and nonhypoxic hydrogel to determine (B) Three-dimensional trajectories of tracked cells (representative trajectories), (C) Overall speed (D) Velocity in the x, y, and z directions; and (E) Mean square displacement (MSD) in the x, y, and z directions. Plots were created using position of KIA-GFP cells in the hydrogels. Significance levels were set at *P<0.05, ^P<0.01 and #P<0.001.
Figure 4B:
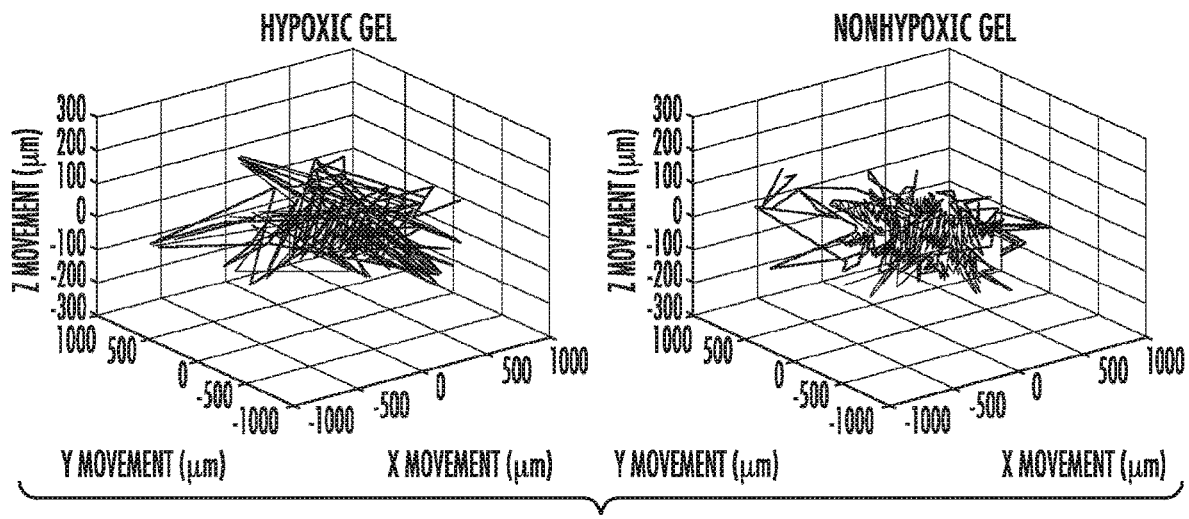
Figure 4C:
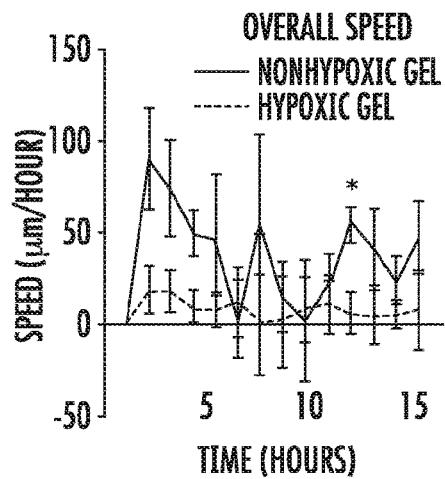
Figure 4D:
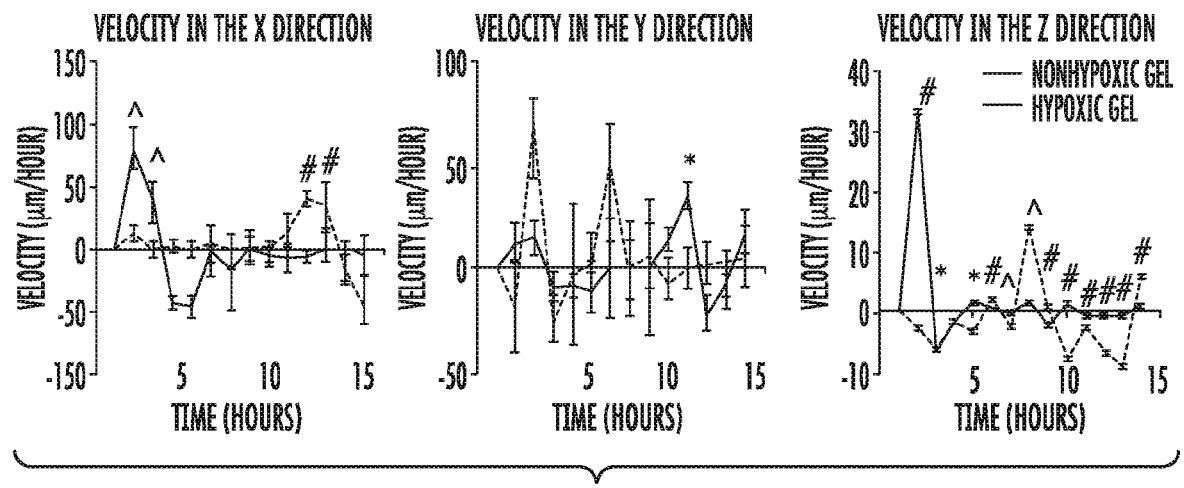
Figure 4E:
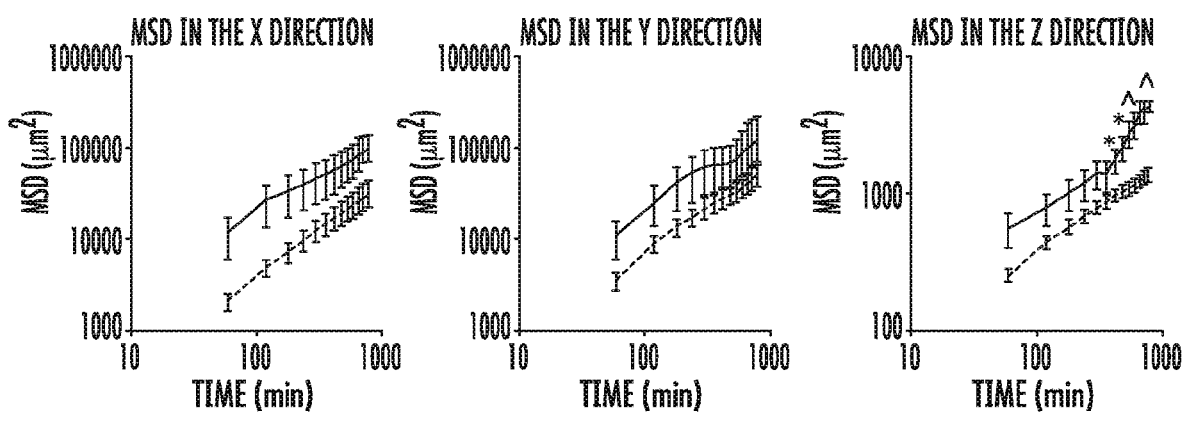

The HI-hydrogel system is designed to create an $O_2$ upward gradient, wherein DO levels increase toward the interface between the construct and $O_2$ saturated culture media. Encapsulation of individual cell suspension would provide the inventors the opportunity to document single-cell movement in relation to the $O_2$ gradient (FIG. 4Ai). As these constructs are cultured in air-oxygenated media, hypoxic and nonhypoxic upward gradients are maintained in each of the gel type. Invasive DO measurements validated hypoxic and non-hypoxic gradients in the hydrogel-cell constructs (FIG. 4Aii). These results confirm that the inventors are able to successfully mimic the gradients seen in the primary tumor in vivo. Thus, we next examined how sarcoma cell motility is regulated by the $O_2$ gradients in the 3D hypoxic and nonhypoxic gradients. We encapsulated KIA-GFP in the HI hydrogels and analyzed movement on day 3 using real-time 3D cell tracking. Upon examining the 3D trajectory profiles of the KIA-GFP encapsulated cells, we observed greater overall cell movement in the hypoxic gradients compared to the nonhypoxic gels (FIG. 4B). We also found that cells in the hypoxic gradient gels are moving faster than those in the nonhypoxic gels. This holds true for the velocity profiles in the x, y, and z directions as well as the overall speed of the cells moving through the gel (FIG. 4C-D). Interestingly, we found that cells also moved in the z-direction, which has not been reported before. Importantly, cell velocity in the z-direction was primarily upwards, in the direction of increased $O_2$ tension (FIG. 4D). We further computed and analyzed the MSD in the three planes. (FIG. 4E). Here too, $O_2$ gradient seem to affect cell motility as indicated by the MSD in the z-direction. Cells exposed to the hypoxic gradients cells are traveling over larger distances compared to those in the nonhypoxic gradients (FIG. 4E). Interestingly, non-gradient hypoxic constructs (i.e. hydrogel constructs cultured in hypoxic conditions) showed slower cell movement and a lower mean squared displacement compared with hypoxic gradient constructs. Overall, this data shows that increased DO levels enhance the speed, distance and direction of sarcoma cell movement.

Inhibiting 3D Hypoxic Gradient Migration.

Figure 5A:
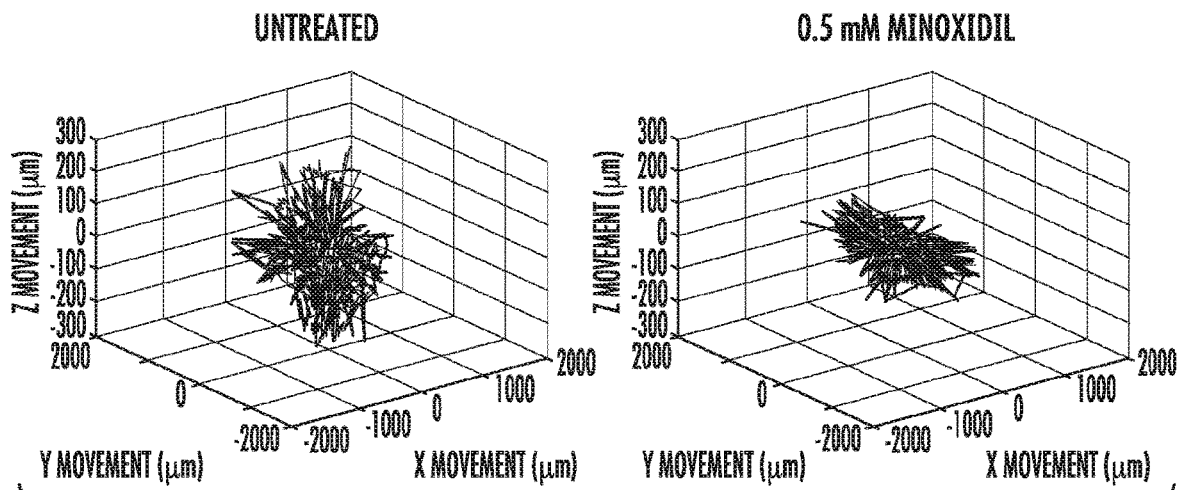
Figure 5B:
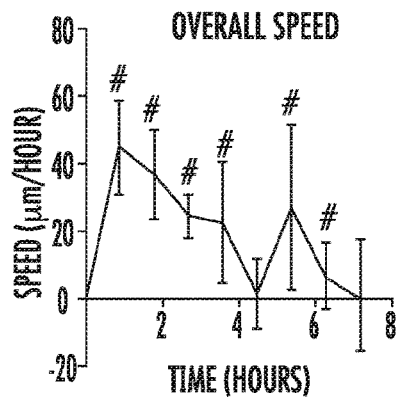
Figure 5C:
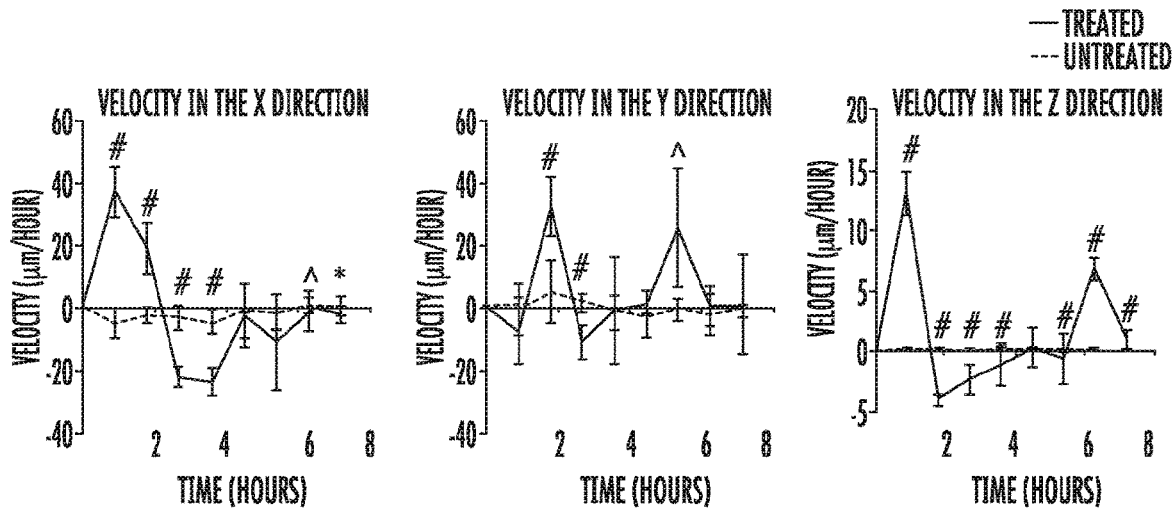
Figure 5D:
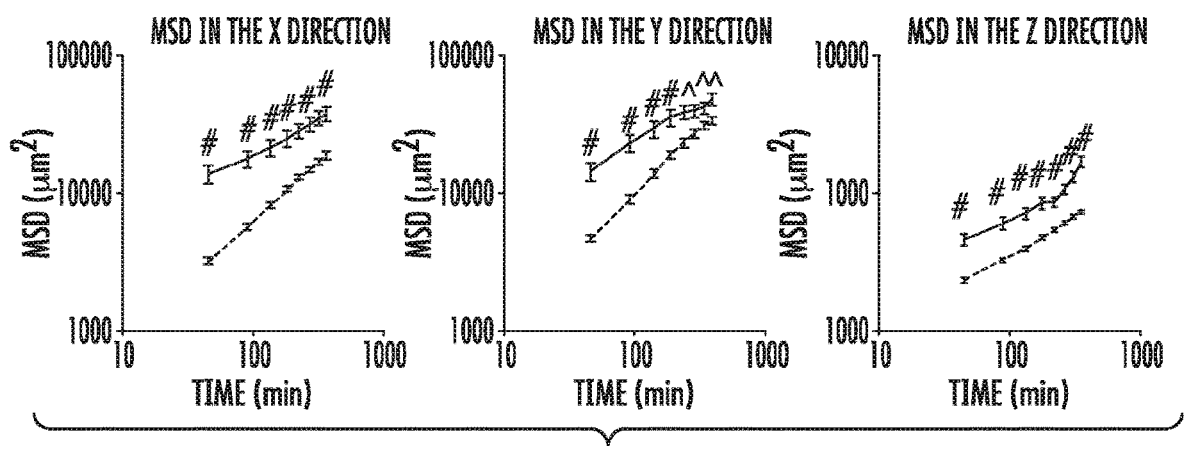
Figure 5G:
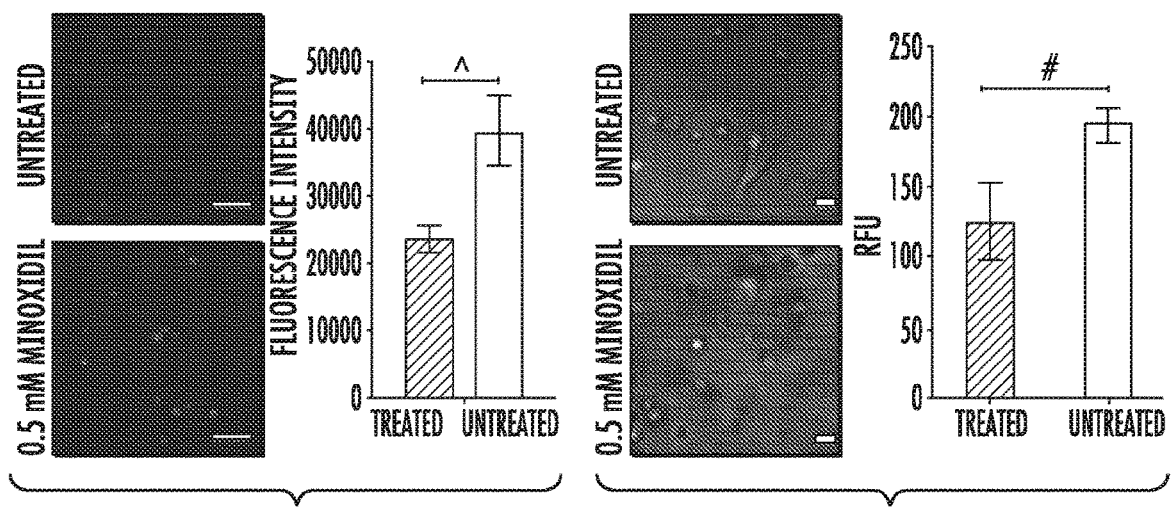
Figure 5G:
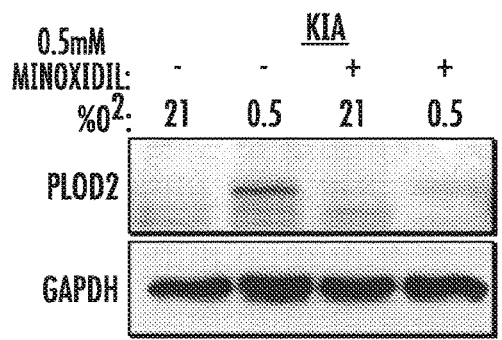
Figure 6A:
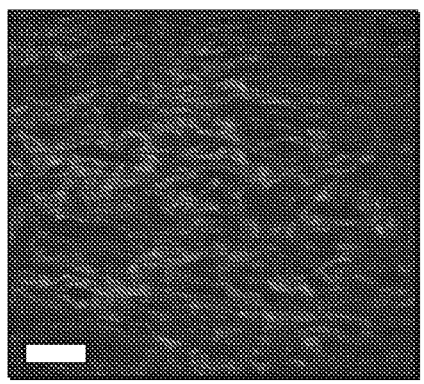
FIG. 6(A)-6(F) illustrates a hypoxic collagen gel. A.) Primary patient sarcoma collagen architecture, which was used to verify in-vitro collagen design. B.) Oxygen data showing the establishment of hypoxic and atmospheric gradients in the system. C.) Seeding technique used in the hypoxic collagen gel system. D.) Cells seeded in the hypoxic collagen gel matrix spreading out in the gel. E.) Cells moving in the hypoxic collagen gels at faster speeds in the z direction. F.) Drug screening data of camptothecin, CRXL101 (nanoparticle form of camptothecin) and DMSO control in collagen gels.
Figure 6B:
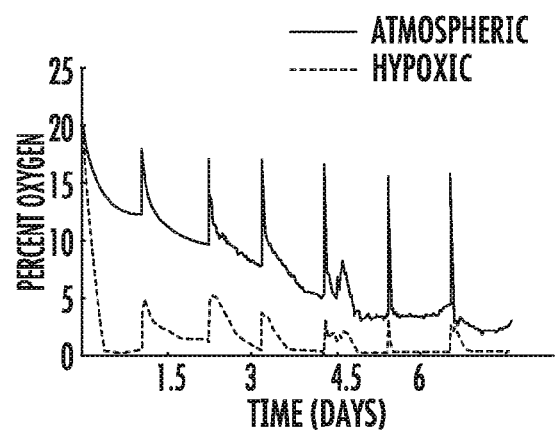
Figure 6C:
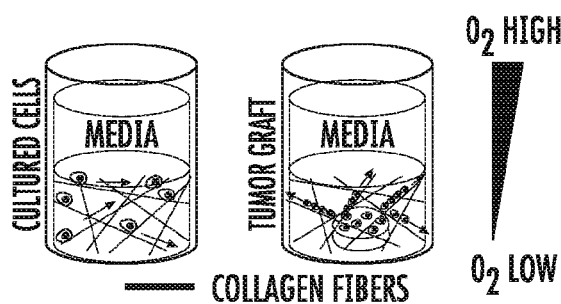
Figure 6D:
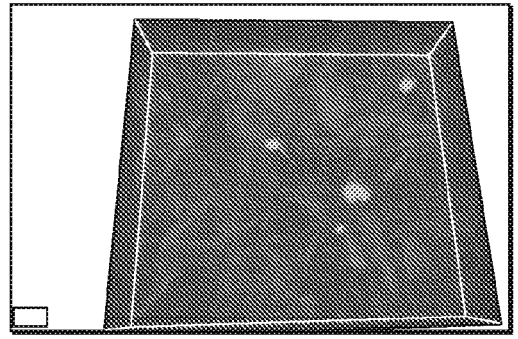
Figure 6E:
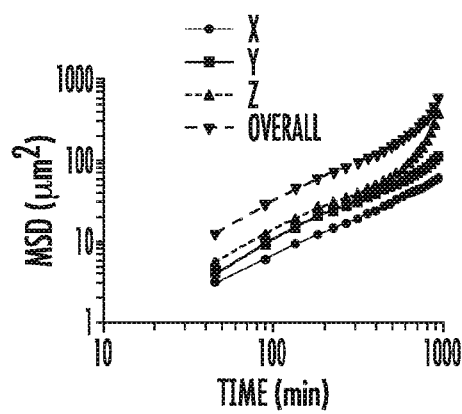
Figure 6F:
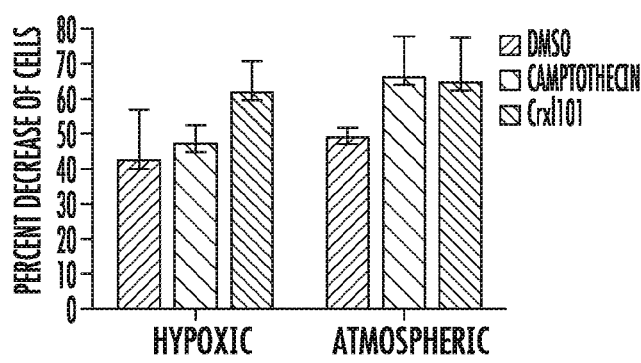

The inventors demonstrated that PLOD2 promotes metastasis in a hypoxia and HIF-1α dependent manner in an in vivo model of UPS. To examine whether the oxygen-controllable hydrogel faithfully represents the intratumoral hypoxic environment, we examined the effect of minoxidil, a pharmacologic inhibitor of PLOD2 expression, on sarcoma cell migration. Minoxidil treatment (0.5 mmol/L) for 12 hours of sarcoma cells encapsulated in the hypoxic hydrogels, significantly reduced KIA cell movement (FIG. 5A) concomitant with reduced overall cell speed as well as velocity and MSD in the x.y. and z directions (FIG. 5B-D). Minoxidil treatment of sarcoma cells encapsulated in the nonhypoxic hydrogels did not significantly affect cell migration in the X and Y directions, with slight inhibition of migration in the z-direction. Examining matrix remodeling, we found that minoxidil treatment reduced collagen deposition (FIG. 5E) and inhibited the proteolytic degradation of the hypoxic matrices (FIG. 5F). As expected, we found that hypoxia-induced PLOD2 expression is inhibited with Minoxidil treatment (FIG. 5G). Together, this data shows that hypoxia gradients determine the direction and speed of sarcoma cell migration in a HIF1/PLOD2 dependent manner. Importantly, these findings also highlight the utility of hydrogel encapsulation assays for the identification of novel therapeutic targets and inhibitors for the treatment of metastatic sarcoma and potentially other cancers as well.

Leveraging our novel $O_2$ controlling hydrogel, we generated a 3D in vitro model that enables us to analyze cancer cell responses to $O_2$ gradients and the effect of small molecule inhibitors. Using this approach, the present invention presents a new concept in which $O_2$ acts as a 3D physico-tactic agent during early stages of sarcoma tumor invasion. The inventors found that an $O_2$ gradient is present in early stages of sarcoma development and that during this stage, cells respond to the hypoxic gradient by aggressively invading the matrix, followed by fast and long-distance migration. Moreover, the present invention demonstrated that in hypoxic gradients individual sarcoma cells not only migrate faster and over a longer distance while remodeling the matrix, they also migrate in the direction of increased $O_2$ tension. Finally, we showed that treatment with minoxidil inhibits the migration and matrix remodeling in the hypoxic gradient. These findings are important for the understanding of the metastatic process and establishing the 3D in vitro model as a platform for testing therapeutic targets and interventions for the treatment of cancer.

Oxygen-Controllable and Hypoxia-Inducible (HI) Hydrogels of the Present Invention.

The oxygen Controllable and Hypoxia-Inducible Hydrogels are described in U.S. application Ser. No. 14/536,392, filed Nov. 7, 2014, and incorporated herein by reference. HI hydrogels can be generated with various phenolic agents (phenol molecules), such as ferulic acid (FA), tyramine (TA), 4-Hydroxyphenylacetic acid, 3-(4-Hydroxyphenyl) propionic acid, Dopamine, Norepinephrine, epinephrine, and their derivatives. Such phenolic agents include the structures in Table 1.

TABLE 1

Phenolic Agents

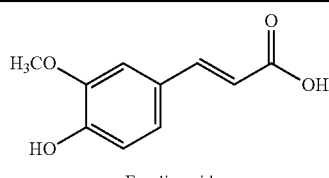

Ferulic acid

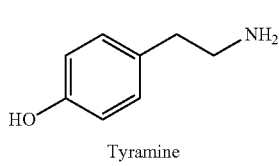

Tyramine

TABLE 1-continued

Phenolic Agents

4-Hydroxyphenylacetic acid 3-(4-Hydroxyphenyl)propionic acid

Dopamine

Norepinephrine epinephrine

The novel HI hydrogels can be generated from natural or synthetic polymers as the polymer backbone. Examples of natural or synthetic polymers include collagen, gelatin, chitosan, heparin, fibrinogen, hyaluronic acid, chondroitin sulfate, pullulan, xylan, dextran, and polyethylene glycol as well as their derivatives. Gelatin (Gtn) is one preferred polymer backbone due to its cell-response properties, including cell adhesion and proteolytic degradability, which are critical in vascular morphogenesis (Hanjaya-Putra, D. et al., *Blood*, 2011; 118:804-815; Davis, G. E. et al., *Circulation research*, 2005; 97:1093-1107). Gtn provides relatively simple functionalization with for example, FA, for the formation of intramural hypoxia for both in vitro and in vivo vascular inductions. This has been further explored as an invasion assay by controlling the level of hypoxia on the gel in order to look at cancer vasculature sprouting (Shen, Yu-I., et al. "Hyaluronic acid hydrogel stiffness and oxygen tension affect cancer cell fate and endothelial sprouting." Biomaterials science 2.5 (2014): 655-665). Dextran is a further preferred polymer backbone, used in conjunction with a hydrophilic linker such as polyethylene glycol (PEG) due to modifiability, bioactivity and hydrophilicity, as well as the similarity of the properties to those of various soft tissues.

The high content of hydroxyl functional groups in the Dex molecule allows the Dex to be converted or modified easily with other molecules. A chain of Dex polymer includes three hydroxyl groups per repeat unit, which can allow for a high degree of substitution (DS) of target molecules (Jin, R. et al., *Biomaterials* 2007, 28, 2791). In addition, Dex has excellent water solubility that enables easy control of the precursor solutions. Some polymers may incorporate adhesion sites, such as Arg-Gly-Asp, and additional degradability features, such as MMP-sensitive peptides, depending on the application (Cuchiara, M. P. et al., *Advanced functional materials*, 2012; 22:4511-4518; Khetan, S. et al., *Nature materials*, 2013; 12:458-465; DeForest, C. A. et al., *Nature materials*, 2009; 8:659-664).

Methods for Forming Oxygen Concentration Gradient Collagen Gel.

In one embodiment, gradient collagen gels are prepared from commercially available rat tail collagen. A tissue culture dish is coated with polyethylenimine (PEI) and glutaraldehyde to increase adhesion to the gel. A combination of 1 M sodium hydroxide (NaOH), M199 10×, M199 1×, and collagen are mixed at a ratio of 1 part NaOH, to 3.15 parts M199 10×, to 68.0275 parts M199 1×, 27.0125 parts collagen (when the starting concentration of collagen is at 9.15 mg/mL). The solution is then incubated on ice as previously described. The collagen gel solution is then mixed with sarcoma cells at a concentration to achieve a final concentration of 2.5 mg/mL of collagen and 2 million cells/mL. The hypoxic gradient is achieved by manipulating the principles of Fick's first law:

$$J = D\frac{\partial c}{\partial z} + R$$

where J is the flux of oxygen through the gel, D is the diffusion coefficient of the gel, dc/dz is change in oxygen concentration per change in height, and R is the cell oxygen consumption rate. By controlling the vessel that the gel is placed in (i.e. polystyrene tissue culture well) we can minimize the diffusion into the hydrogel through the sides and bottom, and only have oxygen transport through the top of the gel. The diffusion of oxygen through the top of the gel is balanced by the consumption oxygen by the cells, allowing a hypoxic gradient to be maintained.

Using Oxygen Concentration Gradient Collagen Gel to Study Cancer.

Cancer metastasis is a poorly understood process that results in 90% of cancer-associated deaths. It has recently become apparent that the tumor microenvironment significantly impacts metastatic progression, through extracellular matrix (ECM) remodeling, stiffness remodeling, cell to cell/matrix interactions, and spatial/chemical gradients. Collagen hydrogels have been used as the traditional in-vitro model for cancer metastasis and growth for and for the study of tumor extra-cellular matrix interactions though other hydrogels maybe used such as hyaluronic acid hydrogels. These collagen gels exhibit typical collagen fibril morphology that is seen in patient tumors and in the standard in-vivo platform (see FIG. 1A). However, this model lacks one of the key principles that is observed in every tumor environment, hypoxia or low oxygen.

A novel hydrogel platform was developed in the present invention to study cancer cell movement and migration. Firstly, collagen gels were generated and verified that by controlling the oxygen diffusion coefficient in the gel and the cell consumption rate, hypoxic gradient hydrogels can be established (see FIG. 1B). Next, cells were encapsulated to examine their behavior within the gel. The goal was to explore the collagen remodeling and cell migration within the platform (see FIG. 1C). In the confocal reflective image (see FIG. 1D), cells were seen sprouting along and interacting with these native collagen fibers in the in-vitro hypoxic collagen gel model of the present invention. Furthermore, it is confirmed that in the hypoxic gel there is a faster migration of the cells in the oxygen gradient direction (FIG. 1E).

These hydrogels were then tested with novel therapeutics that are affected by hypoxia. One of the trends in cancer is to take drugs that have previously failed in the clinic and encapsulate them in nanoparticles to improve their delivery and efficacy. However, while improvement of nano-particled drug performances can be documented in vivo, results in vitro demonstrate equal or lesser efficacy. Camptothecin is a known cancer therapeutic that has failed in the clinic due to the ability of the drug to be inactive once it has been administered intravenously. The inventors have tested a novel compound CRLX101 of Cerulean Pharmaceuticals, which is a nanoparticle encapsulation of camptothecin. From this data (see FIG. 1F), it was demonstrated the higher efficacy of the nanoparticle compared to its small molecule counterpart in hypoxia. This is similar to the clinical data reported by Cerulean. From this data it was demonstrated the capability of this hypoxic collagen gel platform to better physiologically mimic the tumor microenvironment.

Examples/Methods

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation Materials.

Gelatin (Gtn, type A from porcine skin, less than 300 bloom), laccase (lyophilized powder from mushroom, ≥4.0 units/mg), 3-methoxy-4-hydroxycinnamic acid (ferulic acid, FA), N-(3-dimethylaminopropyl)-N'-ethylcarbodiimide hydrochloride (EDC), N-hydroxysuccinimide (NHS), dimethyl sulfoxide (DMSO), and deuterium oxide ($D_2O$) were supplied from Sigma-Aldrich (Saint Louis, Mo.) and used as obtained without purification. Dialysis membrane (molecular cutoff=3500 Da) was purchased from Spectrum Laboratories (Rancho Dominguez, Calif.).

Synthesis of Gtn-HI Hydrogels.

Gelatin-based hypoxia-inducible (Gtn-HI) hydrogels were synthesized by carbodiimide-mediated coupling reaction as we previously reported. Prior to polymer synthesis, the inventors prepared a solvent by mixing DMSO and distilled (DI) water with 1 to 1 volume ratio. The inventors dissolved gelatin (1.0 g) in 50 ml of the solvent at 40° C. FA (0.78 g, 4.0 mmol) was dissolved in 20 ml of the solvent and activated with EDC (0.92 g, 4.8 mmol, 1.2 eq. of carboxyl unit of FA) and NHS (0.64 g, 5.6 mmol, 1.4 eq. of carboxyl unit of FA) at room temperature for 15 minutes to give amine reactive FA molecules. The activated solution was then applied to the Gtn solution and the conjugative chemical reaction was conducted at 40° C. After 24 hours, the reacted solution was dialyzed against DI water using a dialysis membrane (molecular cutoff=3500 Da) for five days. After dialysis, we obtained GtnFA polymers by freeze-drying and kept the product in a refrigerator (below 4° C.) before use. The chemical structure was confirmed using a $^1$H NMR spectrometer (Bruker AMX-300 NMR spectrometer, Billerica, Mass.) and the degree of substitution of FA molecules was measured using an UV/Vis spectrometer (SpectraMax; Molecular Devices, Sunnyvale, Calif.).

Cancer Cell Expansion and Culture within Gtn-HI Hydrogels.

KIA (derived from a genetic murine model of sarcoma, LSL-Kras$^{G12D/+}$; Ink4a/Arf$^{fl/fl}$ as established previously (2), or KIA-GFP or KIA-HIF-1α- or KIA-Scr were expended under standard culture conditions (37° C. and 5% $CO_2$) in high-glucose DMEM with 10% fetal bovine serum (FBS), 1% Penicillin-Streptomycin (PS, Invitrogen) and 1% L-glutamine (Invitrogen). For cancer cell encapsulation, all solutions were prepared using Dulbecco's Phosphate-Buffered Saline (DPBS, Invitrogen) and filtered for sterilization using a syringe filter with a pore size of 0.2 μm. First, we prepared cell pellets of KIA or KIA-GFP or KIA-HIF-1α- or KIA-Scr (1.0×10$^6$ cells) in 1.5 ml eppendorf tubes. The inventors then mixed the pellets with 375 μl of polymer stock solution (4% Gtn-FA solution) by gentle pipetting to give homogeneous cell suspensions and added 125 μl of laccase stock solution (100 U/ml). After mixing the enzyme, the solution was incubated at 37° C. for 2 minutes and then transferred to a 96-well plate (BD Bioscience). The cells were cultured within the hydrogel matrices under standard culture conditions in KIA media. The final concentration of cells, polymers, and laccase were 1.0-2.0×10$^6$ cells/ml, 3%, and 25 U/ml, respectively. The cancer cell morphology was observed by light microscopy (in phase-contrast mode) and fluorescence microscopy (BX60, Olympus, Tokyo, Japan).

Primary Tumor Formation, DO Measurements and Encapsulation.

For primary tumor encapsulation, the inventors generated mouse sarcomas through subcutaneous injection of 1.0×10$^6$ cells/ml of KIA into nude mice. After day 10 we isolated tumors and prepared tumor discs (diameter, 3.0 mm; thickness, 0.4 mm) by biopsy punching. The tumor specimens were encapsulated within the different thickness hydrogels (hypoxic, 2.5 mm, preferably 3 mm thickness; nonhypoxic, 1.25 mm thickness, preferably 1.5 mm). For tumor encapsulation, we first prepared 5 μl of the hydrogel pad (3 w/v % Gtn-HI) on a 96 well plate, and then placed the tumor specimens on the pad. The mixture of polymer and laccase solutions was applied to the wells, and entire hydrogel construct was cultured under standard cell culture conditions (37° C. and 5% $CO_2$) in KIA media (high glucose DMEM with 10% FBS, 1% PS, and 1% L-glutamine) for up to a week. The $O_2$ levels during the culture period were monitored using noninvasive $O_2$ sensors as described above. For quantification of 3D tumor invasion, we took 3-5 images of different regions within the hydrogels using confocal z-stack analysis (>200 μm thickness) and measured the distance from the edge of tumor to the end of the tumor invading the hydrogel matrices using ImageJ software. To monitor real-time tumor invasion and migration, we encapsulated tumors generated from KIA-GFP cells.

Non-Invasive $O_2$ Measurement During Cell and Tumor Graft Culture.

The DO levels were monitored non-invasively at the bottom of hydrogels using commercially available sensor patches (Presens, Regensburg, Germany), as previously established. For DO measurement, the cell suspension (75 μl of polymer and cell suspension) and laccase solution (25 μl of 100 U/ml laccase stock solution) were mixed and incubated for 2 min, and then plated on the $O_2$ sensor attached to a 96-well plate (BD Bioscience). All measurements were performed under standard cell culture conditions (37° C. and 5% $CO_2$) in the culture media. To vary $O_2$ tension, we controlled the thickness of hydrogels in a volume-dependent manner. We generated hydrogels with different minimum dissolved $O_2$ ($DO_{min}$) levels (defined as hypoxic and non-hypoxic gels). For example, to generate hypoxic gels we plated 100 μl (2.5 mm thickness) of a mixture including polymer, cells, and laccase solutions into a well, whereas 50 μl (1.25 mm thickness) of the mixture was plated into the well for preparing nonhypoxic gels.

Invasive $O_2$ Gradient Measurements.

The $O_2$ levels in vivo were measured using Needle-Type Housing Fiber-Optic $O_2$ Microsensor (PreSens, Regensburg, Germany). These needle sensors were mounted on a micromanipulator with 10 μm precision (PreSens). Hydrogel-cell constructs were generated as detailed above. Tumors were generated as previously stated, and DO measurements were performed once tumors were visible. $O_2$ gradient measurements were performed using the needle sensor and a micromanipulator (PreSens). The tumor diameter was measured using a caliper and the needle was placed at the center of the tumor and moved outward in 0.5 mm increments, recording a DO reading at each distance, until reaching the edge of the tumor. The volume of the tumor was calculated using the following equation:

$$V = \tfrac{1}{2} * L * W^2$$

where V is the volume of the tumor, L is the major axis, and W is the minor axis of the tumor. The tumor $O_2$ measurements were averaged and the standard error mean was calculated for each distance from the center of the tumor.

This same approach was used to evaluate the $O_2$ gradient in the hydrogel at day 1, 3, 5 and 7 in the KIA encapsulated samples. It should be noted that in vitro invasive measurements might deviate a little from non-invasive measurements as the insertion of the needle can result in uncontrolled $O_2$ penetration into the hydrogel.

Matrix Degradation, Migration Assays and Drug Treatment.

To assess effect of $O_2$ levels on matrix degradation, we incorporated 10 μg/ml of DQ™ gelatin (Invitrogen) into polymer solutions when preparing cell suspensions, and then mixed with the laccase solution as described above. After day 3, the hydrogels with DQ-gelatin were observed by the fluorescence microscopy (BX60, Olympus, Tokyo, Japan) and quantified by measuring the fluorescence intensity using a fluorescence spectrophotometer at wavelength of 495 nm excitation and 515 nm emission (Molecular Devices).

For the 3D cancer cell migration assay, we encapsulated KIA-GFP cells and tumor grafts in hydrogel to generate constructs with different $O_2$ levels as previously. For non-gradient hydrogel controls, constructs were formed and incubated at 1% oxygen for 3 days and then tracked in that chamber at day 3. Cells were tracked at day 3 using live-cell three-dimensional confocal microscopy (LSM 780, Carl Zeiss, Thornwood, N.Y., USA) equipped with a cell incubator (5% $CO_2$ and 37° C.). In order to properly optimize the experiment only cells that started in frame were included, with a shorter timeframe was used for the tumor encapsulated samples. The time-lapse and z-stack images (>200 μm thickness) were collected every 30 minutes up to 24 hours at five randomly selected positions. The images were analyzed using Imaris spot analysis (Imaris 8.1, Bitplane, South Windsor, Conn., USA) software to track the time-dependent mobility. The 3D migration analysis was performed following the strategy developed by Wirtz and colleagues. A minimum of 100 individual cells at each point were tracked to generate x, y, and z coordinates at each time point. This data was then sorted to only include cells that were present at time zero. From this sorted data the time that the cells were in frame was calculated, and the most common time was used to pick cells for tracking analysis. This was done to maximize the sample size of cells that could be analyzed. Finally, velocity and speed profiles, mean squared displacements, and trajectory plots were calculated using code adapted from Wirtz et al (5, 6) for triplicate tracking trials (n=3) (Matlab, Mathworks Inc.). The statistical analysis was performed using MATLAB (Mathworks Inc.) to calculate the mean, standard deviation and standard error mean. A t-test was performed where appropriate to determine significance (GraphPad Prism 4.02). Graphed data is presented as average±SD. Significance levels were set at: *$P<0.05$; ^$P<0.01$; #$P<0.001$.

For minoxidil treatment, the cells were cultured in hypoxic hydrogels as stated above for three days. On the third day, 0.5 mM minoxidil (dissolved in KIA cell culture media) was added to the wells and the cells were tracked for 24 hours. Untreated cultures served as controls. Cell tracking and data analysis was performed as above.

PLOD2 Western Blot.

Low-oxygen conditions were maintained in a Ruskinn in vivO$_2$ 400 hypoxia work station. Simultaneously, KIA Cells were treated with vehicle or 0.5 mM Minoxidil diluted in DMEM culture media (Sigma Aldrich) for 16 hours. Whole cell lysates were prepared in SDS/Tris pH 7.6 lysis buffer. Proteins were electrophoresed and separated by SDS-PAGE and transferred to nitrocellulose membranes and probed with the following antibodies: rabbit anti-GAPDH (Cell Signaling Inc.), and rabbit anti-PLOD2 (Proteintech).

Rheological Analysis.

To analyze matrix stiffness, the inventors performed rheological analysis of the HI hydrogels using a rheometric fluid spectrometer (RFS3, TA Instruments, New Castle, Del.). In the rheological experiments, tumor constructs cultured within HI hydrogels were plated in the instrument. The inventors performed dynamic time sweep on the samples after day 3 in culture. The inventors monitored the elastic modulus (G') and viscous modulus (G") at 10 percent of strain and a frequency of 0.1 Hz at 37° C. A solvent trap wetted with deionized water was used to prevent sample evaporation.

Gene Expression.

To assess gene expression, we performed quantitative real time RT-PCR as described previously. Total RNA was extracted from cancer cells encapsulated in hydrogels using TRIzol (Invitrogen), according to the manufacturer's instructions. In brief, the inventors placed the hydrogel constructs into 500 μl of TRIzol and homogenized using a micro homogenizer. The suspension was centrifuged at 12,000 G for 15 minutes and the supernatant was separated. The inventors then added 100 μl of chloroform to the solution and mixed manually for 20 seconds. The mixture was centrifuged at 12,000 G for 10 minutes and the supernatant was isolated. The solution was mixed with 250 μl isopropyl alcohol and kept at −4° C. for 1 hour. The precipitates were separated by centrifugation at 7,500 G for 5 minutes and then washed using 70% ethyl alcohol (EtOH). Total RNA was quantified using an ultraviolet (UV) spectrometer and validated by lack of DNA contamination. One microgram of RNA was transcribed using reverse transcriptase M-MLV and oligo(dT) primers (both from Promega, Madison, Wis.), according to the manufacturer's instructions. The inventors used TaqMan Universal PCR MasterMix and Gene Expression Assay (Applied Biosystems, Foster City, Calif.), according to the manufacturer's instructions for LOX, PLOD2, col1A1, and β-actin.

Histological Analysis.

For histological analysis, hydrogel constructs or tumors were harvested and fixed using 3.7% paraformaldehyde and then dehydrated in graded EtOH (80-100%). We then embedded the samples in paraffin blocks and serially sectioned them using a microtome (5 μm). The slides were stained with either haematoxylin or eosin (H&E) or underwent immunohistochemistry for HIF-1α as previously described. For quantification of HIF-1α positive cells in tumor sections, cells expressing nuclear HIF-1α were counted manually from 40× images (n=8). The total number of cells in the images were counted and percent positive cells were calculated. The standard deviation and t-test were performed on the data to determine significance (GraphPad Prism 4.02). Graphed data is presented as average±SD. Significance levels were set at: $P<0.05$; $P<0.01$; *$P<0.001$.

Immunoflorescence Analysis.

Hydrogels were fixed using 3.7% paraformaldehyde and incubated at room temperature for 1 hour. For staining the cells were permabolized with 0.05% Triton-X for 30 minutes, washed with PBS and incubated with primary antibodies over night. The primary antibody used with collagen 1 or HIF-1α (Novous Biologicals, Littleton, Colo.). Certain samples were rinsed with PBS and incubated with Alexa Fluor 546 (1:500; Invitrogen) for 1 hour, followed by incubation with Alexa Fluor 488 Phalloidin (1:40; Invitrogen) for 30 minutes and with 4-6-diamidino-2-phenylindole, DAPI, (1:1000; Roche Diagnostics) for 10 minutes. The labeled cells were examined using fluorescence microscopy (LSM 780, Carl Zeiss, Thornwood, N.Y., USA). Collagen fluorescence intensity was analyzed using ImageJ (ImageJ, National Institutes of Health, Bethesda, Md.).

Statistical Analysis.

All experiments were performed in triplicate for at least 3 biological replicates. We performed RT-PCR analysis in triplicate with duplicate readings. We performed statistical analysis using GraphPad Prism 4.02 (GraphPad Software Inc., La Jolla, Calif.). For all analyses other than the live migration (which its statistics is detailed above), the standard deviation and t-test were performed on the data to determine significance (GraphPad Prism 4.02). Graphed data is presented as average±SD. Significance levels were set at: $P<0.05$; $P<0.01$; *$P<0.001$. All graphical data were reported.

Gradient Collagen Gels.

In one embodiment, gradient collagen gels are prepared from commercially available rat tail collagen. A tissue culture dish is coated with polyethylenimine (PEI) and glutaraldehyde to increase adhesion to the gel. A combination of 1 M sodium hydroxide (NaOH), M199 10×, M199 1×, and collagen are mixed at a ratio of 1 part NaOH, to 3.15 parts M199 10×, to 68.0275 parts M199 1×, 27.0125 parts collagen (when the starting concentration of collagen is at 9.15 mg/mL). The solution is then incubated on ice as previously described. The collagen gel solution is then mixed with sarcoma cells at a concentration to achieve a final concentration of 2.5 mg/mL of collagen and 2 million cells/mL.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of analyzing cell migration comprising:
providing a gel comprising a top, a polymer, and cells;
forming an oxygen gradient within the gel by controlling a balance of the diffusion of oxygen through the top of the gel and of the consumption of oxygen uptake by the cells; and
measuring speed, distance, or direction of cell motility or any combination thereof, thereby analyzing cell migration;
wherein analyzing cell migration comprises immunofluorescent staining of the cells and a fluorescent microscope;
wherein the step of analyzing cell migration quantifies the amount cell migration when comparing the cell migration of the cells with reference cell migration of reference cells in a reference sample.

2. The method of claim 1, wherein the oxygen gradient formed within the gel is in the range of about 0% to 21% of dissolved oxygen content.

3. The method of claim 1, wherein the gel further comprises a bottom and the cells are in the bottom ⅔ of the gel.

4. The method of claim 1, wherein the cells are cancer cells.

5. The method of claim 1, wherein the polymer is selected from the group comprising collagen, gelatin, chitosan, heparin, fibrinogen, hyaluronic acid, chondroitin sulfate, pullulan, xylan, dextran, and polyethylene glycol as well as their derivatives, and combinations thereof.

6. The method of claim 1, wherein the polymer is cross-linked by a cross linking agent selected from the group consisting of physical crosslinkers, chemical crosslinkers, enzyme mediated crosslinkers, peptide based crosslinkers, or a combination thereof.

7. The method of claim 6, wherein the cross linking agent is a phenolic agent selected from ferulic acid (FA), tyramine (TA), 4-Hydroxyphenylacetic acid, 3-(4-Hydroxyphenyl)propionic acid, Dopamine, Norepinephrine, epinephrine, and their derivatives.

8. The method of claim 1, wherein the cells deposit their own extracellular matrix in the gel.

9. The method of claim 1, wherein the oxygen gradient is determined by measuring the concentration of dissolved oxygen in at least two regions of the gel.

10. The method of claim 9, wherein the dissolved oxygen is measured using $O_2$ sensors.

11. A method of identifying agents for treating or preventing cancer comprising:
providing a gel comprising a top, a polymer, and cancer cells;
forming an oxygen gradient by controlling a balance of the diffusion of oxygen through the top of the gel and by the consumption of oxygen uptake by the cancer cells;
applying an agent to the gel; and
comparing a characteristic of the cancer cells in the gel to cancer cells in a reference gel wherein the agent has not been applied to the reference gel, wherein the agent reduces or inhibits the characteristic of the cancer cells in the gel compared to the cancer cells in the reference gel, thereby identifying agents for treating or preventing cancer.

12. The method of claim 11, wherein the oxygen gradient formed is in the range of about 0% to 21% of dissolved oxygen content.

13. The method of claim 11, wherein the gel further comprises a bottom and the cancer cells are near the bottom of the gel.

14. The method of claim 11, wherein the polymer is selected from the group comprising collagen, gelatin, chitosan, heparin, fibrinogen, hyaluronic acid, chondroitin sulfate, pullulan, xylan, dextran, and polyethylene glycol as well as their derivatives.

15. The method of claim 11, wherein the polymer is crosslinked by a cross linking agent selected from the group consisting of physical crosslinkers, chemical crosslinkers, enzyme mediated cross linkers, peptide based crosslinkers, or a combination thereof.

16. The method of claim 15, wherein the cross linking agent is a phenolic agent selected from ferulic acid (FA), tyramine (TA), 4-Hydroxyphenylacetic acid, 3-(4 Hydroxyphenyl)propionic acid, Dopamine, Norepinephrine, epinephrine, and their derivatives.

17. The method of claim 11, wherein the cancer cells are selected from the group comprising sarcoma cells, carcinoma cells, or a combination thereof.

18. The method of claim 11, wherein the cancer cells are obtained from a tumor of an animal or a human subject.

19. The method of claim 11, wherein the cancer cells deposit their own extracellular matrix.

20. The method of claim 11, wherein the characteristic is selected from the group comprising gene expression, protein expression, cytoskeleton organization, nucleus shape, cell shape, ECM secretion and assembly, matrix degradation, matrix remodeling or a combination thereof.

21. The method of claim 11, wherein the characteristic is gene expression, wherein the mRNA expression is measured of a gene selected from the group comprising HIF-1a, ColA1, LOX, PLOD2, or a combination thereof.

22. The method of claim 11, wherein the characteristic is cell migration and the cell migration is determined by taking images of different regions within the hydrogels and using cell tracking to measure the distance from the edge of the tumor to the end of the tumor invading the gel.

23. The method of claim 22, wherein the cell tracking is determined by confocal z-stack analysis.

24. The method of claim 11, wherein the reference hydrogel is a non-hypoxic hydrogel having a dissolved oxygen content of greater than 5%.

25. The method of claim 11, wherein the gel has a thickness in the range of about 1.0 mm to 4.0 mm.

26. The method of claim 11, wherein the agents are selected from the group comprising a capture molecule, protein, peptide, nucleic acid, chemical, or a combination thereof.

27. The method of claim 11, wherein the agent is a capture molecule selected from the group comprising an antibody, an antibody fragment, an aptamer, a monoclonal antibody, or a combination thereof.

* * * * *